(12) United States Patent
Dennerlein et al.

(10) Patent No.: US 9,401,019 B2
(45) Date of Patent: Jul. 26, 2016

(54) IMAGING TOMOSYNTHESIS SYSTEM, IN PARTICULAR MAMMOGRAPHY SYSTEM

(71) Applicant: SIEMENS AKTIENGESELLSCHAFT, Munich (DE)

(72) Inventors: Frank Dennerlein, Eckental (DE); Andreas Fieselmann, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 14/670,750

(22) Filed: Mar. 27, 2015

(65) Prior Publication Data
US 2015/0279064 A1 Oct. 1, 2015

(30) Foreign Application Priority Data

Mar. 27, 2014 (DE) .................. 10 2014 205 756
Mar. 19, 2015 (DE) .................. 10 2015 204 957

(51) Int. Cl.
| | |
|---|---|
| G06K 9/00 | (2006.01) |
| G06T 7/00 | (2006.01) |
| A61B 6/00 | (2006.01) |
| G06T 11/00 | (2006.01) |
| G09G 5/02 | (2006.01) |
| H04N 1/60 | (2006.01) |
| A61B 6/02 | (2006.01) |

(Continued)

(52) U.S. Cl.
CPC .............. *G06T 7/0012* (2013.01); *A61B 6/025* (2013.01); *A61B 6/502* (2013.01); *A61B 6/5205* (2013.01); *G06T 11/006* (2013.01); *G09G 5/02* (2013.01); *H04N 1/6027* (2013.01); *A61B 6/032* (2013.01); *A61B 6/12* (2013.01); *A61B 6/463* (2013.01); *A61B 6/5217* (2013.01); *G06T 2200/24* (2013.01); *G06T 2207/10112* (2013.01); *G06T 2207/30068* (2013.01); *G06T 2207/30196* (2013.01); *G06T 2210/41* (2013.01); *G06T 2211/424* (2013.01); *G06T 2211/436* (2013.01); *G09G 2300/0452* (2013.01); *G09G 2340/08* (2013.01); *G09G 2380/08* (2013.01)

(58) Field of Classification Search
None
See application file for complete search history.

(56) References Cited

U.S. PATENT DOCUMENTS

| | | | |
|---|---|---|---|
| 2003/0156747 A1 | 8/2003 | Faber | |
| 2004/0147927 A1* | 7/2004 | Tsougarakis | ....... A61F 2/30756 606/53 |
| 2005/0135555 A1* | 6/2005 | Claus | ..................... A61B 6/025 378/19 |

(Continued)

OTHER PUBLICATIONS

Wikipedia, "Color Space", found on the Internet May 15, 2015, pp. 1-5, revision Feb. 3, 2014.

(Continued)

*Primary Examiner* — Shervin Nakhjavan
(74) *Attorney, Agent, or Firm* — Laurence Greenberg; Werner Stemer; Ralph Locher

(57) ABSTRACT

An imaging tomosynthesis system, in particular a mammography system, includes a computer system which generates x-ray projections of an examination object from a plurality of projection angles. The system further reconstructs a stack of tomosynthetic slice images, generates at least one overview image of density values of an examination object from the tomosynthetic image data, selects characteristic density values in the stack at at least one plane position, and determines the geometric level of the at least one selected characteristic density value. The overview image is then displayed with a color value correlated to the geometric level of the at least one characteristic density value.

30 Claims, 7 Drawing Sheets

(51) Int. Cl.
 *A61B 6/03* (2006.01)
 *A61B 6/12* (2006.01)

(56) References Cited

U.S. PATENT DOCUMENTS

| | | | |
|---|---|---|---|
| 2007/0286470 A1* | 12/2007 | Bernard | G06T 7/0012 382/132 |
| 2008/0030501 A1* | 2/2008 | Kariathungal | G06T 19/00 345/427 |
| 2008/0155468 A1* | 6/2008 | Rosander | G06F 19/321 715/810 |
| 2009/0016483 A1 | 1/2009 | Kawasaki et al. | |
| 2009/0147074 A1* | 6/2009 | Getty | A61B 6/466 348/51 |
| 2009/0257627 A1* | 10/2009 | Nay | G06T 7/0081 382/128 |
| 2011/0150178 A1 | 6/2011 | Bernard et al. | |
| 2012/0014578 A1* | 1/2012 | Karssemeijer | G06T 7/0012 382/131 |
| 2012/0157819 A1* | 6/2012 | Jerebko | A61B 6/5217 600/407 |
| 2012/0176365 A1 | 7/2012 | Hansegard et al. | |
| 2012/0308095 A1* | 12/2012 | Engel | A61B 6/025 382/128 |
| 2012/0308107 A1* | 12/2012 | Engel | A61B 6/025 382/131 |
| 2013/0064440 A1 | 3/2013 | Wiemker et al. | |
| 2014/0037167 A1 | 2/2014 | Shirahata | |

OTHER PUBLICATIONS

Wikipedia, "Local maximum intensity projection", found on the Internet May 15, 2015, p. 1, revision Sep. 6, 2012.

Smedby, Ö., et al., "Color-coded depth information in volume-rendered Magnetic Resonance Angiography", Society for Optics and Photonics, Medical Imaging, 2004, pp. 669-675.

\* cited by examiner

FIG 5

51 — Calculating a synthetic x-ray image by means of ascertaining a respective density value along a visual line and representing the density values as pixels of an image on a display 52 — Selecting two points of the synthetic x-ray image 53 — Calculating the positions of density values corresponding to the two points and calculating the distance between them 54 — Outputting or displaying the calculated distance

FIG 6
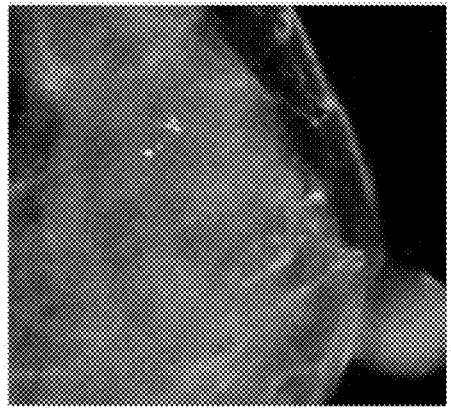
1) User observes synthetic mammogram
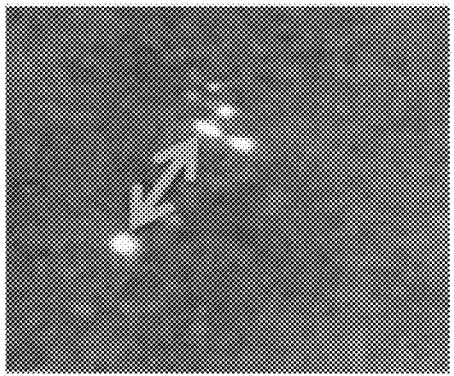
2) User selects two points for distance determination
3) Algorithm ascertains 3D world coordinates on the basis of the values of the MIP-W(u,v) coordinates at the two points
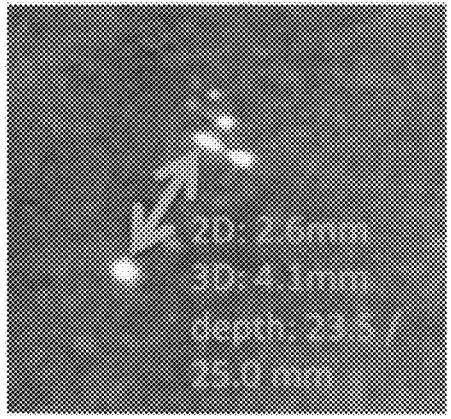
4) The distance ascertained in three dimensions is represented (the two-dimensional distance and the depth are additionally specified)

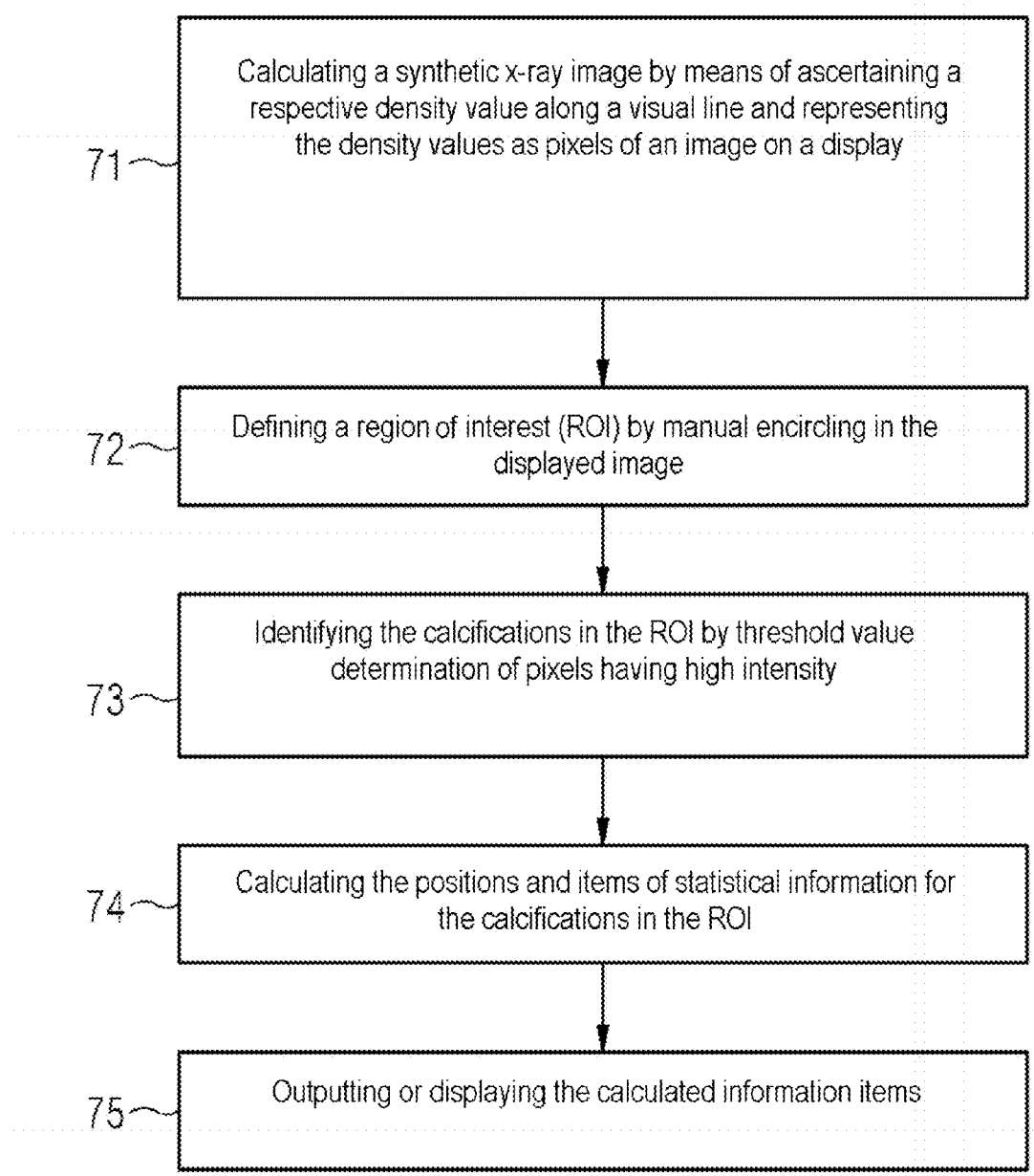

IMAGING TOMOSYNTHESIS SYSTEM, IN PARTICULAR MAMMOGRAPHY SYSTEM

CROSS-REFERENCE TO RELATED APPLICATION

This application claims the priority, under 35 U.S.C. §119, of German patent application DE 10 2014 205 756.6, filed Mar. 27, 2014, and DE 10 2015 204 957.4, filed Mar. 19, 2015; the prior applications are herewith incorporated by reference in their entirety.

BACKGROUND OF THE INVENTION

Field of the Invention

The invention relates to an imaging tomosynthesis system, in particular a mammography system, comprising an emitter/detector system for scanning an examination object from a plurality of projection angles, which are suitable for generating tomosynthetic image data of the examination object, and a computer system comprising at least one display unit and a storage medium for storing programs which carry out at least one tomosynthetic reconstruction.

X-ray technology has become established as a standard method in medical diagnosis. It is based on the fact that x-rays are attenuated by an object in accordance with the absorption properties of the object. The intensity of the x-rays penetrating the object is measured by means of a position-sensitive detector and related to the intensity of the x-rays without an object. The changes in intensity recorded in this way, depending on the recording geometry, represent a measure which yields in particular a statement about the density of the tissue penetrated by the x-rays.

Traditional x-ray technology typically yields projection images in two dimensions that were recorded by means of a surface detector. Conventionally, however, a resolution orthogonally with respect to the detector surface is not possible. Methods that also yield information regarding the third dimension have been developed in the course of the further development of x-ray technology. These methods are based on recording x-ray projections from a multiplicity of different projection directions and reconstructing density values of the object, resolved in three dimensions in voxels, from the attenuation data—also referred to as projections—obtained thereby. Said voxels are usually output with grayscale values corresponding to the density values and can be used for analyzing the object, e.g., by sections of the object being calculated and represented.

The first x-ray modality which enabled the reconstruction of a volume data set was computed tomography. In order to establish projection data, an x-ray source with an opposing detector is in this case usually rotated about an object or patient lying therebetween and tomographic slice images are reconstructed perpendicular to the axis of rotation from the projection data obtained thus over an angular range of 360°, but at least 180° plus the fan angle of the emitter/detector system. A plurality of other x-ray apparatuses that likewise permit three-dimensional reconstruction, e.g. C-arms and mammography apparatuses, exist at the present time. While C-arm systems still enable scanning, which is required for the reconstruction by tomography, over a projection angle range of 180° plus fan angle, angular ranges of significantly less than 180° are scanned in mammography systems. In accordance with the reduced scanning information, a reconstruction according to the tomosynthesis method is carried out for the 3D-reconstruction from projection data from mammography systems. As a result of the reduced scanning information, image data are created with slightly lower quality compared to computed tomography.

Particularly in mammography, particular challenges arise for the representation of data sets obtained by tomosynthesis, said challenges resulting firstly from the fact that only a restricted angular range and thus volume data affected by artifacts are employed, and secondly from the fact that relevant structures, so-called microcalcifications that indicate cancerous tissue, to be represented have a very small size.

Therefore, it is customary to supplement the tissue representations conventionally obtained by tomosynthesis by other, additional representations in order thus to improve or facilitate the diagnosis. By way of example, additional recordings, e.g. by means of digital mammography or full-field digital mammography (FFDM) can be made. Often, the additional recordings are also dispensed with in favor of a lower x-ray dose and, instead, additional recordings are reconstructed from the volume data obtained by tomosynthesis. In this context, this is also referred to as calculated, synthetic mammography recordings or mammograms.

A synthetic mammogram can be produced for one recording angle (typically 0°) or for a multiplicity of recording angles (this is also referred to as a "rotating mammogram"). Producing a synthetic mammogram need not necessarily involve integration or summation of the volume data along visual lines (also designated as "DRR" standing for the expression "digitally reconstructed radiograph"). By way of example, in addition, as a different technique, maximum intensity projection (MIP) is also customary as an image processing method. In the course of maximum intensity projection, three-dimensional volume data sets or image data sets are converted into two-dimensional projection images by the data point with the maximum intensity in each case being selected along the viewing direction, i.e. along the individual visual lines in the projection direction. One field of application is, for example, the representation of CT angiography and magnetic resonance angiography data. In these data, the blood vessels generally have high signal intensities and are therefore imaged with good visibility by maximum intensity projection. Such a method is discussed, for example, in patent application publication US 2013/0064440 A1.

When producing synthetic recordings from volume data sets, it is desirable for the diagnosing physician to acquire a representation, which is as significant as possible, of the many items of information that are relevant to the diagnosis. The application addresses the problem of making a contribution to this.

SUMMARY OF THE INVENTION

The problem is solved by means of an imaging tomosynthesis system, in particular a mammography system, as claimed.

With the above and other objects in view there is provided, in accordance with the invention, an imaging tomosynthesis system, in particular a mammography system, which comprises:

an emitter/detector system for scanning an examination object from a plurality of projection angles and configured for generating tomosynthetic image data of the examination object;

a computer system including at least one display unit and a storage medium for storing program code configured, during operation, to execute the following method:

generating x-ray projections of the examination object by way of the emitter/detector system from a plurality of projection angles, which are suitable for generating tomosynthetic image data from density values of the examination object;

reconstructing a stack of tomosynthetic slice image data, which respectively extend in a plane through the examination object and which correspond to slices at different levels perpendicular to the respective plane, from the x-ray projections;

generating an overview image of density values of the examination object from the tomosynthetic representations;

selecting respectively one characteristic density value in the stack at at least one plane position of the tomosynthetic slice images;

determining a level of the at least one selected characteristic density value; and displaying the overview image of the density values on the at least one display device and simultaneously displaying the level of the at least one characteristic density value as a color value correlated to the level.

In other words, the starting point of the invention is a procedure which involves carrying out a reconstruction of density values from x-ray recordings of an object. In this case, a density value for the representation of the object on a display is determined, wherein a density value along a straight line passing through the reconstructed density values is selected in the course of determining. This selection of a density value can be carried out e.g. according to the maximum of the density values lying on the straight line in such a way that a typical MIP display (MIP=maximum intensity projection) is obtained. In this case, it is possible for the density values to be processed before the maximum is ascertained, e.g. by smoothing being performed, which suppresses effects brought about by noise.

A general concept of the invention is based on the consideration that, in the procedures described above, the position of the selected density value can be used to make available additional information during the representation of the object, said information facilitating the interpretation of the result.

According to the invention, position information may be determined for the selected density value and used for providing and optionally outputting on the display information concerning the density value. Said information can be e.g. the position information itself or some other information obtained with the aid of the position information.

The position information may represent a measure of the distance to a virtual observer, defined e.g. by a point or a plane. Preferably, the virtual observer is defined by the focal point of the x-ray tube used. The distance then corresponds to the distance traversed by an x-ray on the straight line to the position of the selected density value.

In the course of this first configuration, the density value and the position information may be represented in a pixel of the display by coding in values of a color space used for the pixel representation. In this case, the color space can provide a hue and brightness value for representing a pixel, such that hue and brightness value can be used for coding density value and position information.

In the context of a second configuration of the subject matter of the invention, the position information specifies the position of the density value in a fixed coordinate system or a world coordinate system whose origin lies e.g. in the center of the detector.

The position information is determined, for example, if a user selects the density value displayed or represented on the display (e.g. by means of a mouse, wherein upon selection a local extremum can be sought and used as selected density value, in order thus to compensate for inaccuracies of a manual input).

In the case of the second embodiment, it can be provided that a plurality of density values are displayed on the display, and by selecting two density values, distance information concerning the two density values is ascertained, said distance information being displayed or inserted e.g. on the display.

In one variant of the second embodiment, an image formed on the basis of determined density values is displayed on the display. A region of displayed density values can then be selected on the image, e.g. by encircling by means of a computer mouse. Afterward, in the region density values are identified according to a criterion for the magnitude of the density, e.g. a threshold value. Whether by recourse to the values themselves or by means of the pixel coding thereof, this may take place e.g. in relation to the brightness of the pixel. The items of position information may be determined for the identified density values. The items of position information may be used to determine in three dimensions boundary surfaces including the identified density values. In this case, therefore, a type of box enclosing the density values, or any closed boundary surface which is preferably concave throughout, is formed. The boundary surfaces can be used for representing a region containing the identified density values during the display of density values determined by means of selection along a straight line passing through the reconstructed density values and/or of reconstructed density values.

Both embodiments can also be used jointly or have recourse in part to elements of the respective other embodiment.

Once more in summary, the above and other objects are achieved, in accordance with the invention, by an imaging tomosynthesis system, in particular a mammography system, which comprises:

an emitter/detector system for scanning an examination object from a plurality of projection angles, which are suitable for generating tomosynthetic image data of the examination object, a computer system comprising at least one display unit and a storage medium for storing programs which are configured in such a way that, during operation, they carry out the following method:

generating x-ray projections of an examination object by means of an emitter/detector system from a plurality of projection angles, which are suitable for generating tomosynthetic image data from density values of the examination object, reconstructing a stack of tomosynthetic slice image data, which respectively extend in a plane through the examination object and which correspond to slices at different levels perpendicular to the planes, from the x-ray projections, generating an overview image of density values of the examination object from the tomosynthetic representations, selecting respectively one characteristic density value in the stack at at least one plane position (=image position in the 2D-space of the slice plane) of the tomosynthetic slice images, determining the level of the at least one selected characteristic density value, displaying the overview image of density values on a display device and simultaneously displaying the level of the at least one characteristic density value as a color value correlated to the level.

In respect of definitions, it should be noted that the plane positions should be understood to mean the xy-coordinates of the tomosynthetic slice images in the xy-plane which are equivalent to the xy-plane of the detector or of the overview image. Moreover, the level of the density value is understood to be the value of the z-coordinate at which the density value occurs in the image stack which is stacked one above the other in the z-direction. In the simplest form, the level corresponds to the number of the tomosynthetic slice plane of a numbered stack of tomosynthetic slice images through the examination object. The xyz-coordinates are in this case considered to be coordinates of an orthogonal coordinate system.

What is achieved by such a simultaneous representation of a two-dimensional virtual overview image of density values of an examination object on the basis of the tomosynthetic image data combined with level specifications (=z-position specifications), depicted in color, of characteristic density values is a particularly clear and diagnostically relevant view of relevant density values from a tomosynthetic display, in particular a mammographic display of a female breast.

Advantageously, a MIP (maximum intensity projection) display which, as a as matter of principle, is known in the field of virtually generated overview displays can be selected as an overview image. Here, it is particularly expedient for the characteristic density value also to be selected according to the MIP method, i.e. if the characteristic density values represent the maximum density values at the respective plane position.

Furthermore, it can be expedient if a switching element is available, which makes available the switching on and off of the color information in respect of the level of the characteristic density values. Such a switching element can, for example, be implemented purely by means of software, e.g. as a button to be clicked, or else as a mechanical switch on the display device or on the operating console, possibly in conjunction with a touchscreen.

It can also be particularly advantageous if the density values of the overview display and the level of the at least one characteristic density value can be represented by a code in a selected color space. In particular, the density values and the level in a pixel can be represented by coding in values of a color space used for the pixel representation, wherein, preferably, color values and brightness values are used for representing a pixel in such a way that brightness values are assigned to the density and color values are assigned to the level. In particular, one of the following color spaces can be used as a color space: HSV color space, HSB color space, HSI color space.

In a further embodiment of the tomosynthesis system according to the invention, it is possible that only the plane positions with maximum density values above a prescribed threshold are displayed with the additional level information. Essentially, such an embodiment provides for, where possible, only microcalcifications, which are distinguished by particularly high density values, to be explicitly colored in respect of the level position thereof, while other, less interesting regions are still only displayed with grayscale values. Within the scope of mammography, this leads to a particularly clear display fixed on calcifications. Then, it is particularly advantageous if the system provides a user interface, by means of which it is possible to influence or enter the threshold. Such an interface can be a manually adjustable potentiometer or else a slider or the like displayed on the display. Alternatively, by clicking on density values on the display, this also includes the possibility of setting the threshold in accordance with the clicked-on density value.

In a further embodiment, the tomosynthesis system can be equipped with a user interface for simultaneously selecting at least two plane positions in the overview display, wherein, by selecting two plane positions with characteristic density values, the three-dimensional distance between the spatial positions of the characteristic density values is determined and displayed.

In an even further variant of the embodiment of the tomosynthesis system, provision can be made for a region of displayed density values to be selectable in the overview display, the density values present in this region to be identified, and boundary surfaces which enclose the positions of the identified density values to be determined in three dimensions. If such boundary surfaces are displayed in the overview display, it is easy to identify accumulations of calcifications which, diagnostically, could indicate possible carcinogenic developments.

Here, the boundary surfaces can advantageously be used for displaying a region containing the identified density values when displaying density values established by means of selection along a straight line passing through the reconstructed density values and/or reconstructed density values.

In principle, reference is made to the fact that the scope of the invention also includes the method described here for processing image data and the illustration thereof, wherein a data medium with a computer program written thereon, which executes the steps of this method during operation is likewise part of the invention.

Other features which are considered as characteristic for the invention are set forth in the appended claims.

Although the invention is illustrated and described herein as embodied in an imaging tomosynthesis system, in particular a mammography system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 5 shows a flow chart for a second exemplary embodiment of the invention;

FIG. 6 shows the insertion of additional items of distance information in accordance with the second exemplary embodiment of the invention; and FIG. 7 shows a further flow chart for one variant of the second exemplary embodiment of the invention.

DETAILED DESCRIPTION OF THE INVENTION

Figure 1:
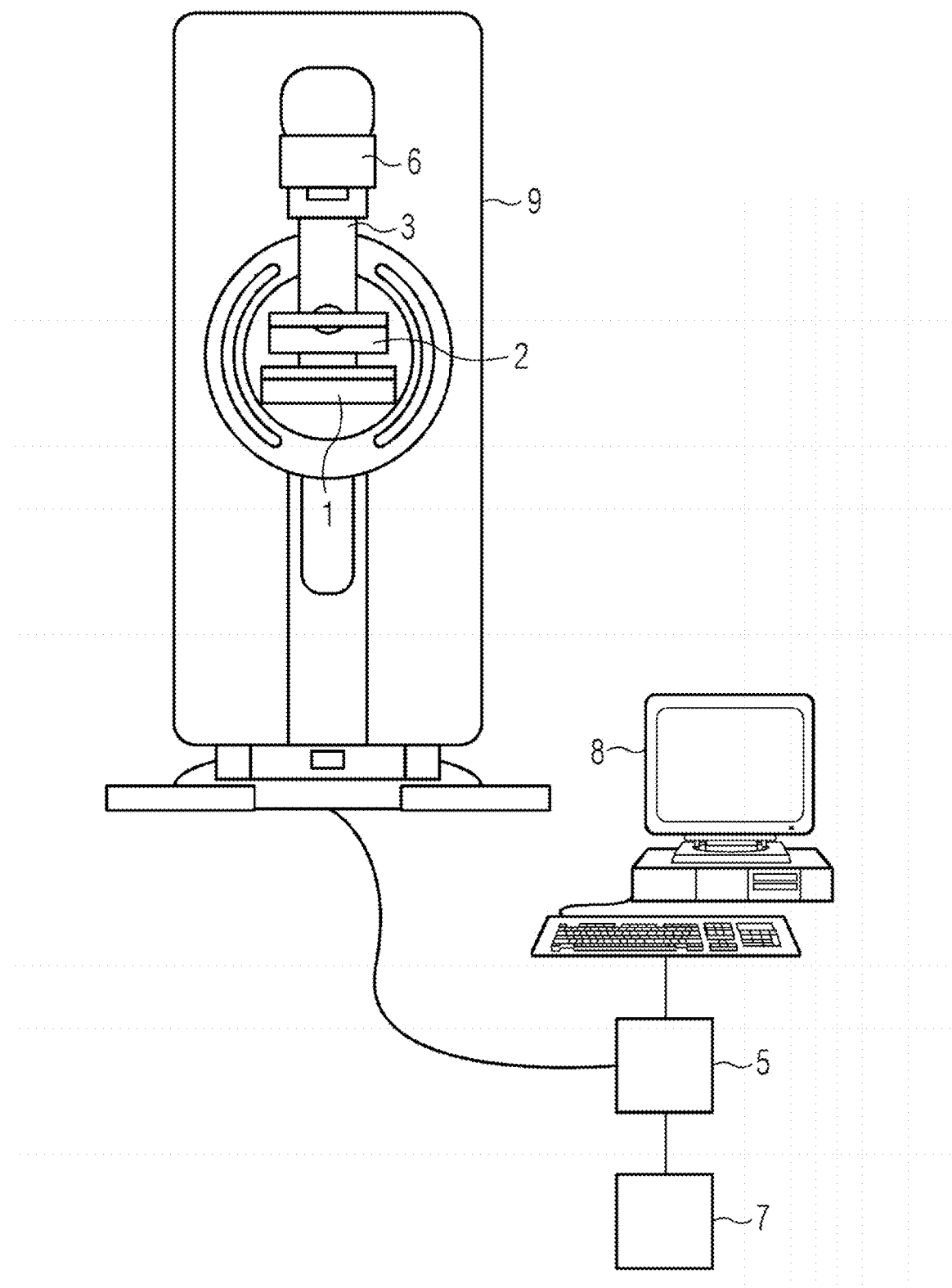
FIG. 1 shows a frontal view of a mammography apparatus.

The following description of an exemplary embodiment of the invention uses the following reference numerals, symbols and acronyms:

1: object table with detector;
2: compression plate;
3: holder;
5: evaluation computer;
6: emitter;
7: storage unit;
8: monitor;
9: mammography apparatus;
10: examination object/female breast;
31-34, 51-54, 71-75: method steps;
101-120: focus positions;
A, B, C: calcification/macrocalcification;
$h_{alt}$: overall height of the examination object the z-direction;
R101-R120: x-ray beam from the focus positions 101-120; and
ROI: region of interest.

Referring now to the figures of the drawing in detail and first, particularly, to FIG. 1 thereof, there is shown a frontal view of a mammography apparatus 9. An object table 1, usually containing the detector, and a compression plate 2, by means of which a breast 10 to be examined (see FIG. 2) is compressed, are arranged on a mount 3. For tomosynthesis recordings, the radiation emitter 6 is embodied as rotatable about a rotation axis orthogonal to the plane of the drawing. Recorded projections can be fed to an evaluation computer 5. Said evaluation computer 5 serves for image reconstruction and for implementing the invention, for example. For this purpose, it is normally connected to a display unit or a monitor 8 for displaying calculated images, and also has a storage unit 7, in which computer programs, parameters and filters according to the invention, that is to say auxiliary variables for calculation and similar variables, can also be stored, which are carried out or used during operation.

Figure 2:
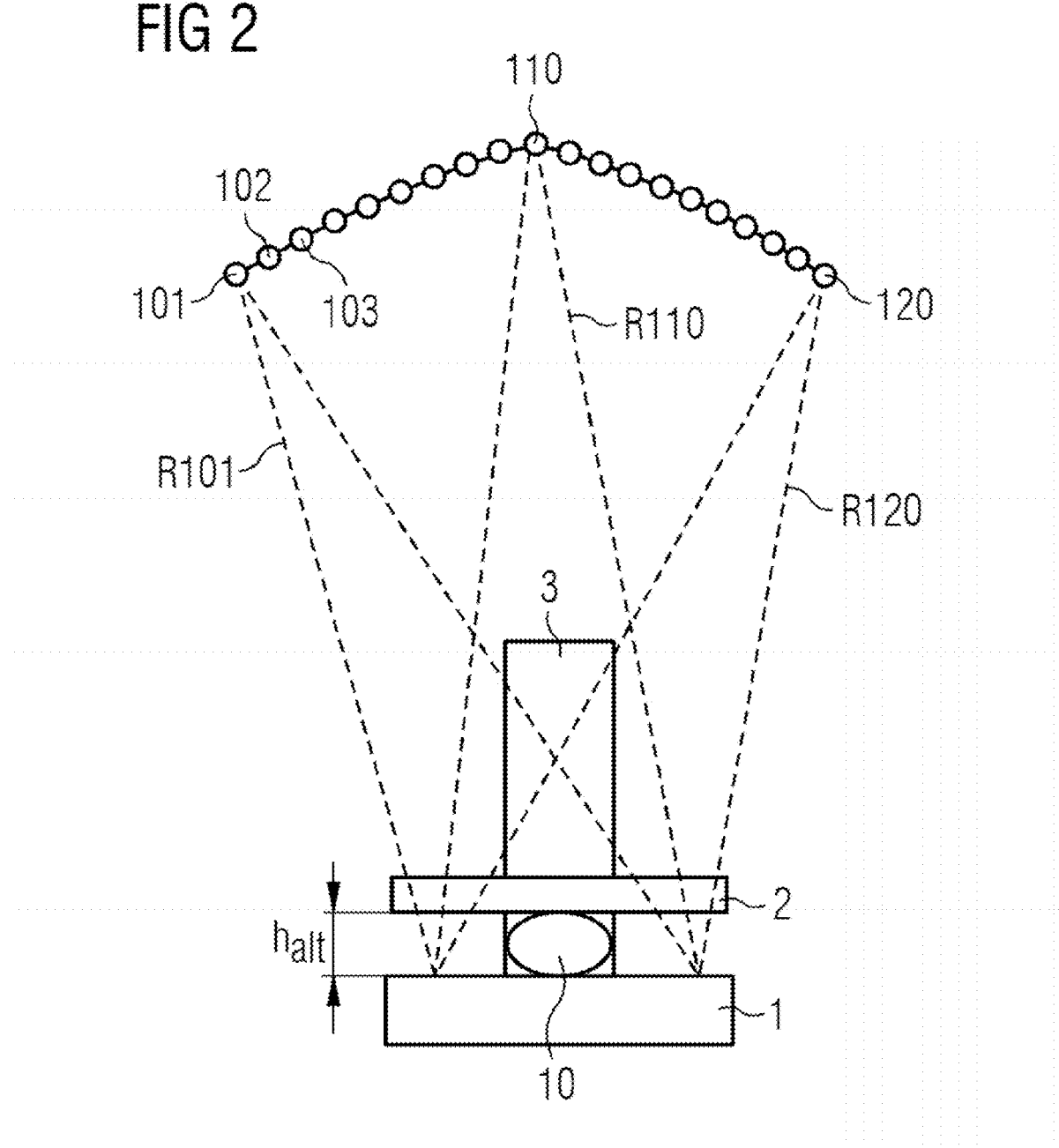
FIG. 2 shows a schematic illustration of a conventional tomosynthesis recording.

The general situation in the case of tomosynthesis recordings is illustrated in FIG. 2. Owing to the recordings from different angular positions (typically minus 25° to plus 25°), the compression plate 2 is configured such that it is wider than for conventional recordings. The x-ray source or the radiation emitter (reference sign 6 in FIG. 1) traverses a trajectory during a tomosynthesis recording of an object, in this case a breast 10. Positions 101, 102, 103 . . . are marked on the trajectory, for each of which positions an x-ray recording is made. These positions reproduce e.g. the location of the focus of the x-ray source during these recordings. The expanding x-ray beam is depicted for three positions 101, 110 and 120. The shape of the x-ray beam is a fan or a cone in most cases.

A volume data set is reconstructed from the recorded projections. Said volume data set is also designated hereinafter as DBT volume (DBT: digital breast tomosynthesis). Customary reconstruction methods are filtered back projection (FBP) e.g. by means of the Feldkamp algorithm and iterative methods. The volume data set is usually present in the form of voxels, which are assigned to spatial points which represent density values which are usually represented as gray-scale values. The analysis involves (at least) mapping these density values in space onto values defined in two dimensions (often designated as pixels), which are used for display on a monitor. Visual lines are typically taken as a starting point in this case. A pixel for display on a monitor is determined from the values of the volume data set along a visual line.

The invention is based on the fact that a density value is selected along the visual lines penetrating through the reconstructed volume data set. This can involve the density maximum along the line (maximum intensity projection or MIP method). This is not absolutely necessary, however, other criteria for selecting the density value may also be selected. It suffices if a position can be assigned to a determined density value. The determined density values directly or in processed form influence pixels of a virtual overview display, i.e. of a synthetic mammogram, which can be displayed on a display or a monitor. For the sake of simplicity, the invention is described for maximum intensity projections (i.e. in the context of the MIP method) hereinafter.

The variables MIP-I(u,v) and MIP-D(u,v) are introduced for the sake of better illustration. These variables are generated by means of the reconstructed DTB volume and are defined as follows.

MIP-I(u,v): R2→R1 (I=intensity): The algorithm runs through a beam from the focus of the x-ray tube used for the recording as far as the projection plane of the synthetic mammogram through the reconstructed tomosynthesis volume. That voxel having the maximum density or intensity which is found in the process is used as a pixel value having the coordinates—in this case u,v, sometimes also referred to as X,Y, the coordinates being taken at the point of intersection of the beam with the projection plane.

MIP-D(u,v): R2→R1 (D=distance): The distance from the focal point to the position of the maximum along the beam is designated by MIP-D. The value for MIP-D is stored with the detector coordinate (u,v) which corresponds to the position at which the beam intersects the detector.

Figure 3:
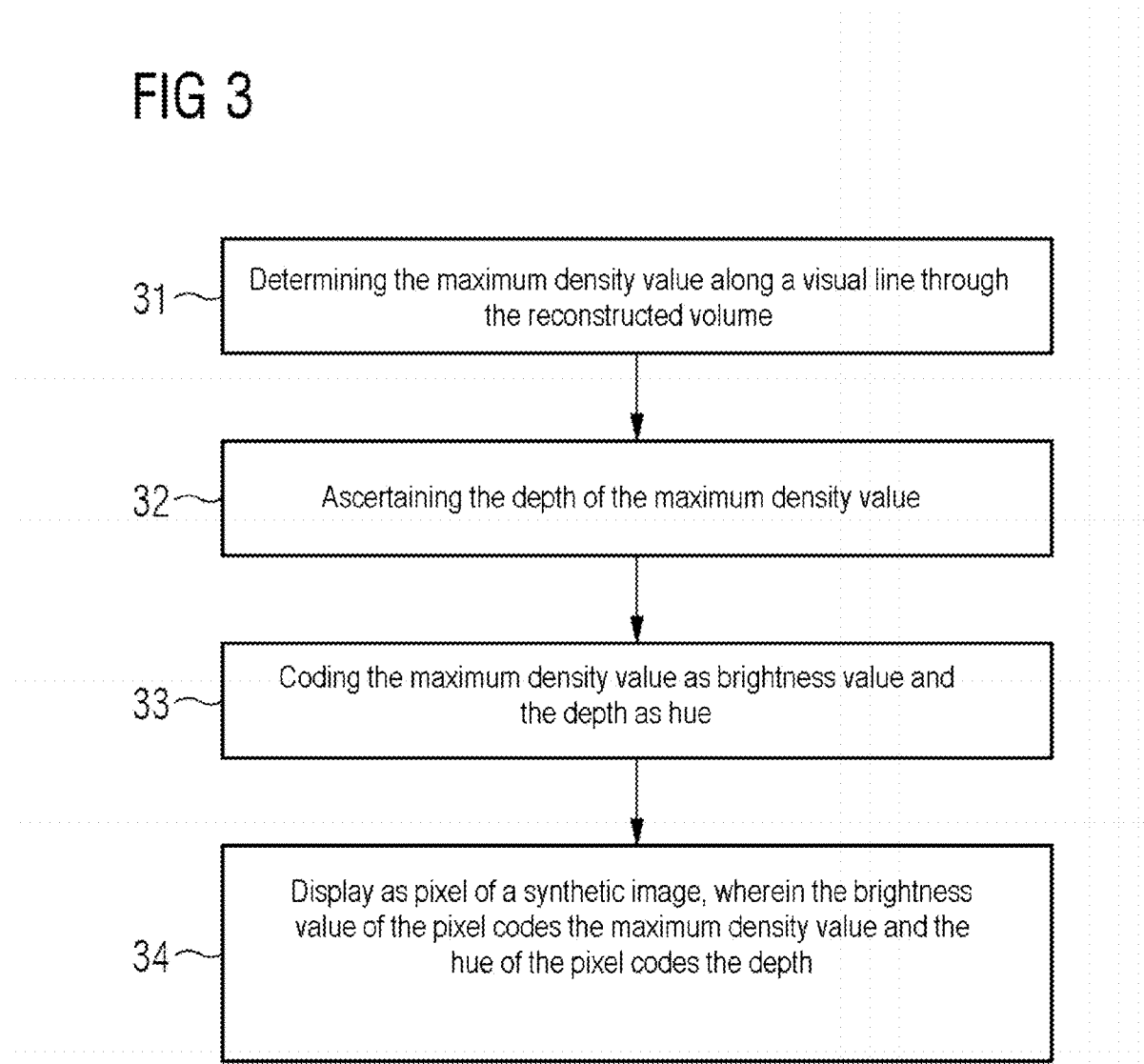
FIG. 3 shows a flow chart for a first exemplary embodiment of the invention.

A central concept of this first embodiment of the invention is that of fusing MIP-I and MIP-D in order to generate an image that yields both the maximum intensity/density and a presentation of the relative distance from objects, in particular from calcifications. This concept is illustrated schematically in FIG. 3. A first step 31 involves ascertaining the maximum density value along a visual line through the reconstructed volume. In addition, the depth of the maximum density value is also determined in a second step 32. A coding of the maximum density value as brightness value and of the depth as hue is carried out (step 33). Finally, step 34 involves displaying the result as a pixel of a synthetic image, wherein the brightness value of the pixel codes the maximum density value and the hue of the pixel codes the depth.

By way of example, an HSV color space can be used for the coding. In the HSV color space, the spatial points are defined with the aid of the hue, the color saturation and the brightness value or light value or dark level (value). An HSL color space, an HSB color space and an HSI color space could also be used instead of an HSV color space. In the context of the exemplary embodiment, the color information is used to code the depth information. The color range is ideally restricted in order that the radiologist is not distracted too greatly by an excessively colorful appearance.

It is possible to provide for the color information to be switched on and off selectively, possibly in a range-dependent manner.

The fusion of the two items of information MIP-I and MIP-D, usually normalized to a value range of 0 to 1, into one image can be carried out as follows:

In the HSV color space, MIP-I is allocated to the "V" channel. That is to say that the maximum density value (MIP-I) is represented by the brightness of the image.

In the HSV color space, the "H" channel is set to values defined by a function dependent on the variable MIP-D. One possible example for this function is H(MIP-D(u,v))=(MIP-D(u,v))0.5.

Other (linear and nonlinear) functions are conceivable, of course. In this way, the position of the maximum (MIP-P) is coded by the color of the image.

In the HSV color space, the "S" channel can be set to a constant value (e.g. 0.5). It should be noted here that it would also be possible to use MIP-I and/or MIP-D to define the "S" value, i.e. the saturation of the image.

Figure 4:
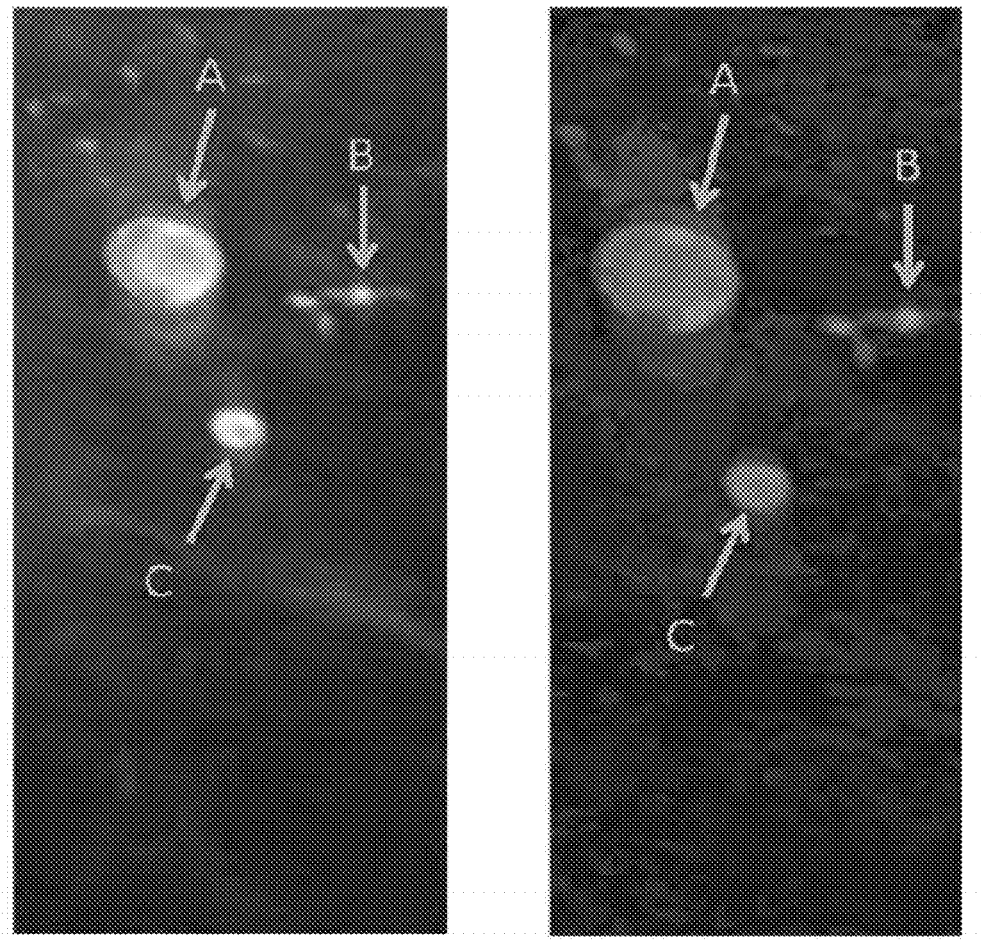
FIG. 4 shows an image obtained in accordance with the first exemplary embodiment.

FIG. 4 shows one example of a synthetic mammogram with color-coded depth information. In that case, the microcalcification A is at a depth comparable to the smaller calcifications B. By contrast, the microcalcification C is at a somewhat different depth than the smaller calcifications B.

One possible workflow that can be carried out by the radiologist in practice is presented below. The color-coded depth information yields additional information for the radiologist. The workflow may be configured as follows:

The radiologist first looks at the gray-scale values of the synthetic mammogram.

The color-coded synthetic mammogram is represented by activation by means of an operator interface. The radiologist can thus better ascertain the spatial distribution of the calcifications and of similar structures.

The radiologist analyzes the reconstructed tomosynthesis sections. The previously acquired knowledge resulting from viewing the synthetic mammogram and the color-coded depth information help the radiologist to focus on structures of interest.

It should be noted that the color-coded synthetic mammogram can be converted to a mammogram consisting of gray-scale values by means of the "H" and "S" channels being set to 0. In this regard, by way of example, in order to save memory space, just the color-coded synthetic mammograms could be stored.

A further advantage of this procedure is that color monitors which can be used with mammography images are sold commercially. The EizoRadiForce RX840-MG monitor, for example, is a color monitor having FDA510(k) approval for mammography.

A second exemplary embodiment is presented below. The basic procedure of a first variant is shown in FIG. 5, where a step 51 involves calculating a synthetic x-ray image by means of ascertaining a respective density value along a visual line and representing the density values as pixels of an image on a display. A next step 52 involves selecting or choosing two points of the synthetic x-ray image. Afterward, step 53 involves carrying out a calculation of the positions of density values corresponding to the two points and calculating the distance between them. Finally, the last step 54 involves outputting or displaying the calculated distance.

The variables MIP-I(u,v) and MIP-W(u,v) are introduced for a more accurate description of this exemplary embodiment. In this case, the variable MIP-I(u,v) is defined as in the first exemplary embodiment. The variable MIP-W(u,v) is defined as follows.

MIP-W(u,v): $R^2 \rightarrow R^3$ (W=world): This variable codes the position of the maximum along the beam in a world coordinate system or a spatially fixed coordinate system. The origin of the coordinate system can lie e.g. in the center of the detector. Since MIP-W has entries relating to three dimensions, a Euclidian distance can be calculated.

With these generated variables MIP-I and MIP-W, a workflow is proposed which allows the actual three-dimensional distance to be calculated.

The density or intensity image MIP-I (possibly supplemented by further image processing or by association with other image contents, such as e.g. DRRs, etc.) is represented for the radiologist on a display.

Two different scenarios are then conceivable:

A. In order to ascertain a distance determination between two points on the represented image, the following procedure is adopted:

Two points in the image are clicked on, for example two projecting calcifications in accordance with MIP-I.

If there is a great variation of the depth coordinates in the vicinity of the location clicked on by the user, it is particularly important where the measurement point is placed. In this case, by way of example, the point with the highest intensity (CALC in FIG. 6) in the vicinity could be selected.

The Euclidian distance between two selected points is calculated by means of the MIP-W coordinates and the actual three-dimensional distance is displayed on the screen. For better comprehensibility, the distance can be split into a distance within the plane and a depth distance and can be displayed in this form.

This is illustrated in more precise detail again in FIG. 6. In the image on the left, the user observes the synthetic mammogram. One image further, the user selects two points for the distance determination. In step 3, an algorithm is used for accessing the three-dimensional world coordinates on the basis of MIP-W(u,v) at the two points. Step 4 involves carrying out the three-dimensional distance determination and displaying it on the display. The two-dimensional distance within the plane and the depth (ascertained perpendicularly to the plane) are also specified in the present case.

B. A second variant of the second embodiment concerns the measurement of a calcification cluster, i.e. of an accumulation of calcifications (FIG. 7).

An ROI (region of interest) is drawn by hand around a calcification cluster in the represented MIP/MIP/I (step 72 in FIG. 7).

An algorithm identifies the calcifications in the region to be defined, i.e. the points having the highest intensity with regard to the MIP-I variable (step 73).

The algorithm then collects all three-dimensional world coordinate information items for all detected calcifications in the cluster and generates a flexible three-dimensional bounding box that includes the three-dimensional point cloud (step 74).

Items of statistical information (size, shape) of the calcifications within said box are calculated and displayed on the screen (step 75).

Since the measurement points and the confining box are in world coordinates, the reconstructed tomosynthesis sections can easily be additionally inserted in order thus to ensure better comparability.

Thus, overall, the invention proposes an imaging tomosynthesis system, in particular a mammography system, which is equipped with a computer system which generates x-ray projections of an examination object from a plurality of projection angles, reconstructs a stack of tomosynthetic slice images, generates at least one overview image of density values of an examination object therefrom, selects characteristic density values in the stack at at least one plane position, determines the geometric level, preferably perpendicular to the slice image plane, of the at least one selected characteristic density value, and displays the overview image with a color value correlated to the geometric level of the at least one characteristic density value by virtue of the density and level values, combined in a pixel-by-pixel manner, being output to the input of a display unit.

Although the invention was illustrated more closely and described in detail by the preferred exemplary embodiments, the invention is not restricted by the disclosed examples and other variations can be derived herefrom by a person skilled in the art, without departing from the scope of protection of the invention. In particular, the invention is not restricted to the feature combinations specified below, but other combinations and partial combinations, which, according to a person skilled in the art, can obviously be carried out, can also be formed from the disclosed features.

The invention claimed is:

1. An imaging tomosynthesis system, comprising:
an emitter/detector system for scanning an examination object from a plurality of projection angles and configured for generating tomosynthetic image data of the examination object;
a computer system including at least one display unit and a storage medium for storing program code configured, during operation, to execute the following method:
generating x-ray projections of the examination object by way of the emitter/detector system from a plurality of projection angles, which are suitable for generating tomosynthetic image data from density values of the examination object;
reconstructing a stack of tomosynthetic slice image data, which respectively extend in a plane through the examination object and which correspond to slices at different levels perpendicular to the respective plane, from the x-ray projections;
generating an overview image of density values of the examination object from the tomosynthetic representations;
selecting respectively one characteristic density value in the stack at at least one plane position of the tomosynthetic slice images;
determining a level of the at least one selected characteristic density value;
wherein the density values and the level are represented in a pixel by coding in values of a color space used for the pixel representation; and
displaying the overview image of the density values on the at least one display device and simultaneously displaying the level of the at least one characteristic density value as a color value correlated to the level.

2. The imaging tomosynthesis system according to claim 1, wherein the overview image is an MIP (maximum intensity projection) display.

3. The imaging tomosynthesis system according to claim 1, wherein the characteristic density values are maximum density values at the respective plane position.

4. The imaging tomosynthesis system according to claim 1, which comprises a switching element enabling the color information in respect of the level of the characteristic density values to be selectively switched on or off.

5. The imaging tomosynthesis system according to claim 1, wherein the density values and the level of the at least one characteristic density value are represented as code in a color space.

6. The imaging tomosynthesis system according to claim 1, wherein the color space provides hues and brightness values for the representation of a pixel, with brightness values being assigned to the density and hues being assigned to the level.

7. The imaging tomosynthesis system according to claim 6, wherein the color space is selected from the group of color spaces consisting of an HSV color space, an HSB color space and an HSI color space.

8. The imaging tomosynthesis system according to claim 1, which comprises a user interface for selecting at least two plane positions in the overview display.

9. The imaging tomosynthesis system according to claim 8, wherein, by selecting two plane positions with characteristic density values, the three-dimensional distance between the spatial positions of the characteristic density values is determined and displayed.

10. The imaging tomosynthesis system according to claim 8, wherein:
an operator is enabled to select a region of displayed density values on the overview display;
said computer system is configured to identify density values that are present in the selected region; and
to ascertain boundary surfaces in three dimensions that include the positions of the identified density values.

11. The imaging tomosynthesis system according to claim 10, wherein the boundary surfaces are used for representing a region containing the identified density values during the display of density values determined by way of selection along a straight line passing through the reconstructed density values and/or of reconstructed density values.

12. The imaging tomosynthesis system according to claim 1 configured as a mammography system.

13. An imaging tomosynthesis system, comprising:
an emitter/detector system for scanning an examination object from a plurality of projection angles and configured for generating tomosynthetic image data of the examination object;
a computer system including at least one display unit and a storage medium for storing program code configured, during operation, to execute the following method:
generating x-ray projections of the examination object by way of the emitter/detector system from a plurality of projection angles, which are suitable for generating tomosynthetic image data from density values of the examination object;
reconstructing a stack of tomosynthetic slice image data, which respectively extend in a plane through the examination object and which correspond to slices at different levels perpendicular to the respective plane, from the x-ray projections;
generating an overview image of density values of the examination object from the tomosynthetic representations;
selecting respectively one characteristic density value in the stack at at least one plane position of the tomosynthetic slice images;
determining a level of the at least one selected characteristic density value; and
displaying the overview image of the density values on the at least one display device and simultaneously displaying the level of the at least one characteristic density value as a color value correlated to the level, and thereby displaying only the plane positions with maximum density values above a prescribed threshold with the additional level information.

14. The imaging tomosynthesis system according to claim 13, which comprises a user interface for entering the prescribed threshold.

15. The imaging tomosynthesis system according to claim 13, which comprises a user interface for selecting at least two plane positions in the overview display.

16. The imaging tomosynthesis system according to claim 13, wherein the overview image is an MIP (maximum intensity projection) display.

17. The imaging tomosynthesis system according to claim 13, wherein the characteristic density values are maximum density values at the respective plane position.

18. The imaging tomosynthesis system according to claim 13, which comprises a switching element enabling the color information in respect of the level of the characteristic density values to be selectively switched on or off.

19. The imaging tomosynthesis system according to claim 13, wherein the density values and the level of the at least one characteristic density value are represented as code in a color space.

20. An imaging tomosynthesis system, comprising:
an emitter/detector system for scanning an examination object from a plurality of projection angles and configured for generating tomosynthetic image data of the examination object;
a computer system including at least one display unit and a storage medium for storing program code configured, during operation, to execute the following method:
generating x-ray projections of the examination object by way of the emitter/detector system from a plurality of projection angles, which are suitable for generating tomosynthetic image data from density values of the examination object;
reconstructing a stack of tomosynthetic slice image data, which respectively extend in a plane through the examination object and which correspond to slices at different levels perpendicular to the respective plane, from the x-ray projections;
generating an overview image of density values of the examination object from the tomosynthetic representations;
selecting respectively one characteristic density value in the stack at at least one plane position of the tomosynthetic slice images;
determining a level of the at least one selected characteristic density value; and
displaying the overview image of the density values on the at least one display device and simultaneously displaying the level of the at least one characteristic density value as a color value correlated to the level; and
a user interface for selecting at least two plane positions in the overview display, wherein, by selecting two plane positions with characteristic density values, the three-dimensional distance between the spatial positions of the characteristic density values is determined and displayed.

21. The imaging tomosynthesis system according to claim 20, wherein the overview image is an MIP (maximum intensity projection) display.

22. The imaging tomosynthesis system according to claim 20, wherein the characteristic density values are maximum density values at the respective plane position.

23. The imaging tomosynthesis system according to claim 20, which comprises a switching element enabling the color information in respect of the level of the characteristic density values to be selectively switched on or off.

24. The imaging tomosynthesis system according to claim 20, wherein the density values and the level of the at least one characteristic density value are represented as code in a color space.

25. An imaging tomosynthesis system, comprising:
an emitter/detector system for scanning an examination object from a plurality of projection angles and configured for generating tomosynthetic image data of the examination object;
a computer system including at least one display unit and a storage medium for storing program code configured, during operation, to execute the following method:
generating x-ray projections of the examination object by way of the emitter/detector system from a plurality of projection angles, which are suitable for generating tomosynthetic image data from density values of the examination object;
reconstructing a stack of tomosynthetic slice image data, which respectively extend in a plane through the examination object and which correspond to slices at different levels perpendicular to the respective plane, from the x-ray projections;
generating an overview image of density values of the examination object from the tomosynthetic representations;
selecting respectively one characteristic density value in the stack at at least one plane position of the tomosynthetic slice images;
determining a level of the at least one selected characteristic density value; and
displaying the overview image of the density values on the at least one display device and simultaneously displaying the level of the at least one characteristic density value as a color value correlated to the level; and
a user interface for selecting at least two plane positions in the overview display, wherein:
an operator is enabled to select a region of displayed density values on the overview display;
said computer system is configured to identify density values that are present in the selected region; and
to ascertain boundary surfaces in three dimensions that include the positions of the identified density values.

26. The imaging tomosynthesis system according to claim 25, wherein the boundary surfaces are used for representing a region containing the identified density values during the display of density values determined by way of selection along a straight line passing through the reconstructed density values and/or of reconstructed density values.

27. The imaging tomosynthesis system according to claim 25, wherein the overview image is an MIP (maximum intensity projection) display.

28. The imaging tomosynthesis system according to claim 25, wherein the characteristic density values are maximum density values at the respective plane position.

29. The imaging tomosynthesis system according to claim 25, which comprises a switching element enabling the color information in respect of the level of the characteristic density values to be selectively switched on or off.

30. The imaging tomosynthesis system according to claim 25, wherein the density values and the level of the at least one characteristic density value are represented as code in a color space.

* * * * *